(12) United States Patent
Vigil

(10) Patent No.: US 6,623,451 B2
(45) Date of Patent: *Sep. 23, 2003

(54) FOLDING SPRING FOR A CATHETER BALLOON

(75) Inventor: Dennis M. Vigil, San Diego, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/202,361

(22) Filed: Jul. 26, 2002

(65) Prior Publication Data

US 2002/0183779 A1 Dec. 5, 2002

Related U.S. Application Data

(63) Continuation-in-part of application No. 09/847,096, filed on May 1, 2001, now Pat. No. 6,425,882.

(51) Int. Cl.[7] .............................................. A61M 29/00
(52) U.S. Cl. ................. 604/99.01; 604/103.14
(58) Field of Search ...................... 604/96.01, 99.01, 604/103, 103.03, 103.08, 103.09, 103.14, 103.13, 104–106; 623/1.11, 1.15; 606/108, 192, 194, 200

(56) References Cited

U.S. PATENT DOCUMENTS

| | | |
|---|---|---|
| 1,967,318 A | 7/1934 | Monahan |
| 4,141,364 A | 2/1979 | Schultze |
| 4,406,656 A | 9/1983 | Hattler et al. |
| 4,787,388 A | 11/1988 | Hofmann |
| 5,015,231 A | 5/1991 | Keith et al. |
| 5,108,418 A | 4/1992 | Lefebvre |
| 5,209,799 A | 5/1993 | Vigil |
| 5,221,261 A | 6/1993 | Termin et al. |
| 5,226,887 A | 7/1993 | Farr et al. |
| 5,681,522 A | 10/1997 | Roychowdhury |
| 5,693,089 A | 12/1997 | Inoue |
| 5,820,613 A | 10/1998 | Van Werven-Franssen |
| 6,001,118 A | 12/1999 | Daniel et al. |
| 6,007,558 A | 12/1999 | Ravenscroft et al. |
| 6,126,652 A | 10/2000 | McLeod et al. |
| 6,224,625 B1 | 5/2001 | Jayaraman |

*Primary Examiner*—Sharon Kennedy
(74) *Attorney, Agent, or Firm*—Nydegger & Associates

(57) ABSTRACT

A device for folding a balloon of a balloon catheter during balloon deflation includes a band and a plurality of elongated fingers that are attached to the band. The band includes a midsection and a pair of overlaps with each overlap extending from the midsection to a respective end of the band. The band is folded into an annulus wherein the overlaps are juxtaposed and can be joined together by soldering, welding or adhesive bonding. The annulus is attached to the catheter tube of the balloon catheter with the fingers extending over the balloon in a substantially same axial direction. In operation, the fingers are moveable between an unstressed configuration, when the balloon is deflated, and a stressed configuration, when the balloon is inflated. In a stressed configuration, the fingers urge against the balloon and are biased toward the stressed configuration to return to an unstressed configuration.

20 Claims, 4 Drawing Sheets

FOLDING SPRING FOR A CATHETER BALLOON

This application is a continuation-in-part of application Ser. No. 09/847,096 filed May 1, 2001, now U.S. Pat. No. 6,425,882. The contents of U.S. Pat. No. 6,425,882 are incorporated herein by reference.

FIELD OF THE INVENTION

The present invention pertains generally to devices and methods for use in the manufacture of balloon catheters. More particularly, the present invention pertains to devices which fold a balloon onto a catheter tube during the deflation of the balloon. The present invention particularly, though not exclusively, pertains to springs which can fold the balloon of a dilatation balloon catheter in an uniform and predictable manner during balloon deflation.

BACKGROUND OF THE INVENTION

Arterial blockages caused by the build up of plaque in the arteries of a patient can have grave consequences. Specifically, the build up of plaque in arteries can reduce and eventually block blood flow through the affected vessel. When blood flow is reduced, the heart muscle is deprived of oxygen, and the patient is prone to suffer angina. In severe cases of artery blockage, the patient can suffer a heart attack.

Many modern surgical techniques have been developed to alleviate the stenoses that are formed when plaque builds up in a patient's arteries. For example, a large number of balloon angioplasty devices exist for relieving arterial stenoses by compression of the stenosis. In several respects, balloon angioplasty devices afford numerous advantages over alternative methods. Foremost among these advantages is that open heart bypass surgery can often be avoided by using angioplasty surgical techniques to relieve stenoses in the arteries that supply blood to the heart. For obvious reasons, it is preferable to avoid open heart surgery when possible because such surgery, as is well known, is invasive and can consequently require significant post-operative recovery time. Accordingly, it is preferable to use relatively simpler angioplasty surgical procedures when such procedures are feasible. Importantly, angioplasty procedures are efficacious in the peripheral arteries as well as in the arteries that supply blood to the heart.

In angioplasty surgery, the balloon of a balloon catheter is initially attached to a catheter tube in a deflated configuration and the catheter tube connects a fluid source in fluid communication with the balloon. The balloon is then positioned at the desired location in the affected artery by advancing the catheter through the artery until the balloon is positioned next to the stenosis that is to be treated. Once the balloon has been properly positioned, fluid is infused into the balloon within the artery. As the balloon expands, it dilates the lumen of the artery and compresses the plaque. Upon being compressed, the plaque may break up or flatten out against the arterial wall. The balloon is then subsequently deflated and, once in its deflated configuration, it is either withdrawn from the artery or placed across another stenosis, to restore normal blood flow through the artery.

A particular problem associated with an angioplasty procedure exists during the deflation stage of the balloon, prior to its removal from the artery. Specifically, it is desirable that the balloon be deflated as tightly as practicable to facilitate its removal from the arterial passageways. In any case, the key to removing the balloon catheter with ease is having the balloon collapse evenly and compactly during balloon deflation. Once deflated, the balloon catheter must often travel through tortuous passageways and it is, therefore, important for the balloon to deflate uniformly into a predictable configuration. If the balloon fails to deflate in an uniform manner, an irregular bulge in the balloon may cause difficulties in withdrawing the balloon catheter from the artery.

Various techniques and balloon constructions have been developed to encourage the balloon to deflate in an uniform manner. For example, U.S. Pat. No. 5,350,361 which issued to Tsukashima et al. for an invention entitled "Tri-fold Balloon For Dilatation Catheter and Related Method" discloses a balloon that is constructed with tri-fold flaps. Such flaps are subjected to heat treatment so that when the balloon deflates, the same fold flaps will form allowing the balloon to return to its original deflated configuration. Another example is a balloon catheter with a means to axially twist the inflatable balloon to reduce the diameter of the balloon for passage through the artery. Such a balloon catheter is disclosed in U.S. Pat. No. 4,292,974 which issued to Fogarty et al. for an invention entitled "Dilatation Catheter Apparatus and Method."

There is, however, a continuing need for improved ways of deflating the balloon of a balloon catheter in a predictable manner for its removal from the artery. The present invention also recognizes the importance of collapsing a balloon evenly onto a catheter tube during balloon deflation so that the balloon catheter can be easily removed from the patient's body without causing damage to the artery. The present invention recognizes the need for an approach that is reliable and predictable. For example, when metals (which have beneficial spring properties) are used to collapse the balloon, several factors must be considered to ensure that the resulting collapsing system is reliable. First, it is important that the metal be corrosion resistant and biocompatible. In this regard, stainless steel is corrosion resistant and has a successful history in invasive medical device applications. Nickel-Titanium alloys such as Nitinol are also suitable for invasive medical device applications.

Another important factor that must be considered when using metals is the strength and reliability of any metal joints that must be made when fabricating a metal article such as a folding spring. In greater detail, the strength and reliability of a metal joint depends on the size and configuration of the joint and the joining method. Thus, when designing a joint to be strong and reliable, it is important to maximize the surface area to be joined and to use a suitable joining method. It is also important that the joining method be easy to use and inexpensive to reduce manufacturing costs. In this regard, the present invention recognizes that soldering and spot welding, when used in conjunction with the proper joint size and configuration, are capable of producing strong reliable joints while minimizing manufacturing costs.

In light of the above, it is an object of the present invention to provide a device and method for manufacturing a device that is useful for folding a balloon predictably and compactly onto a catheter tube during balloon deflation to facilitate removal of the balloon catheter from a patient's body. Another object of the present invention is to provide a device and method for manufacturing a device that is useful for maintaining the balloon tightly wrapped on a balloon catheter when the balloon is in a deflated configuration. It is yet another object of the present invention is to provide a folding spring for a balloon catheter having a strong and reliable metal joint to ensure the reliability of the folding spring. Yet another object of the present invention is to provide a folding spring for a balloon catheter which is relatively simple to manufacture, easy to use, and comparatively cost effective.

SUMMARY OF THE PREFERRED EMBODIMENTS

The present invention is directed to a device and a method for manufacturing a device for folding a balloon of a dilatation balloon catheter during balloon deflation. For the present invention, the device includes a band and a plurality of elongated fingers that are attached to the band.

Each finger in the device of the present invention has a first end and a second end, with the first end being attached to the band and the second end extending away from the band. In their extension, the fingers are substantially parallel to each other and the second end of each finger is rounded. Importantly, the device of the present invention has at least three such fingers. Further, the band of the present invention is formed with a tab and a notch and the length of the band corresponds with the diameter of the catheter tube. When the band is folded, the tab and notch are engaged with each other to form an annulus. Once engaged, the tab and notch can be bonded or soldered to each other or welded together to strengthen the joint between the tab and notch. Thus, the annulus can be considered as being centered on an axis with the fingers extending therefrom in a substantially same axial direction In another embodiment of the present invention, the band includes a midsection and a pair of overlaps with each overlap extending from the midsection to a respective end of the band. When the band is folded into an annulus, the overlaps are juxtaposed. With this cooperation of structure, the overlaps can be joined together by soldering, welding or adhesive bonding. In a particular embodiment, each overlap is formed as a cantilever having a substantially constant thickness. In another embodiment, each overlap is formed as a tapered extension having a substantially uniform transition from the midsection to a respective band end.

The band, when it is formed as an annulus, is attached to the catheter tube of a balloon catheter by well known means, such as by using any appropriate bonding solvent. This is done with the fingers extending from the annulus over the balloon. In one embodiment of the present invention, the annulus is mounted on the catheter tube proximal to the balloon with the fingers extending in a distal direction over the balloon. Alternatively, the annulus can be mounted on the catheter tube distal to the balloon with the fingers extending in a proximal direction over the balloon. In yet another embodiment, an annulus can be mounted respectively at each end of the balloon. Importantly, in all embodiments of the present invention, the rounded ends of the fingers provide a smooth interface with the balloon to prevent them from penetrating into the balloon.

Unlike the band, which is bonded to the catheter tube, the fingers in the device of the present invention are not bonded to the balloon. Instead, they are allowed to slide on the surface of the balloon. Also, they are biased to be moved between an unstressed configuration, when the balloon is deflated and a stressed configuration, when the balloon is inflated. More specifically, in the unstressed configuration, the fingers extend at a slight angle from the annulus with an inclination toward the axis of the catheter tube. On the other hand, in the stressed configuration, the fingers are inclined away from the axis as the fingers extend over the surface of the inflated balloon.

In the manufacture of the device of the present invention, it is preferred that the band and fingers be stamped out from a single flat sheet of stainless steel. Further, prior to attaching the band onto the catheter tube, the fingers are heat treated or heat set. As a result, the fingers, when they are in their unstressed configuration, are inclined at a slight angle toward the axis to keep the balloon in its deflated configuration. Thus, whenever the balloon is deflated, the reduction of fluid pressure in the balloon during deflation will cause the fingers to return to their unstressed configuration. This causes the fingers to urge against the balloon to guide the balloon onto the catheter tube in a predictable configuration.

In the operation of the present invention, the band is first attached to the catheter tube with the fingers, in their unstressed configuration, extending over the deflated balloon. As the balloon is infused with fluid, the fingers expand away from the axis following the surface of the inflated balloon. Although the fingers will follow the expansion of the inflating balloon, the increasing stress in the fingers will cause the fingers to urge against the balloon, pressuring it to collapse back onto the catheter tube. Stated in another way, the fingers are biased in their stressed configuration to return to their unstressed configuration. Once the fluid begins to be removed from the balloon, the fingers will urge the balloon into a predetermined configuration as the fingers return to their unstressed configuration. Once the balloon is deflated and once the fingers return to their unstressed configuration, the balloon catheter may then be removed from the artery.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
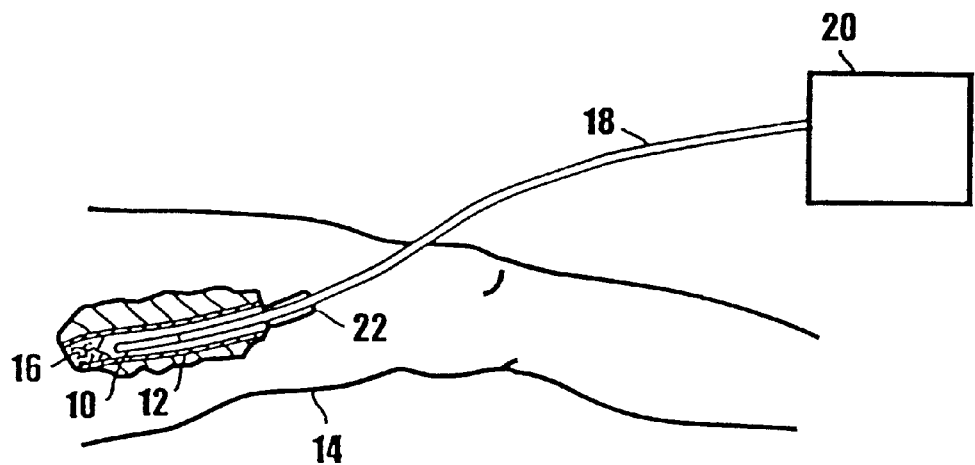
FIG. 1 is a perspective view of a balloon catheter that incorporates the device of the present invention, with the catheter shown in its intended environment while the balloon is in a deflated configuration.

Referring initially to FIG. 1, an angioplasty balloon in accordance with this present invention is shown and is generally designated 10. As shown, balloon 10 is insertable into an artery 12 of a patient 14 for the purpose of relieving an arterial plaque stenosis 16. To this end, FIG. 1 shows that balloon 10 is connected in fluid communication with a hollow catheter tube 18. Catheter tube 18 is in turn connected to a fluid source 20 for infusing fluid into balloon 10, to thereby expand balloon 10 against the stenosis 16. If required, the balloon 10, along with catheter tube 18, can be inserted into the patient 14 through an insertion catheter 22. For the present invention, balloon 10 is preferably made of any suitable angioplasty balloon material, such as polyethylene terephthalate or polyetherimide.

Figure 2:
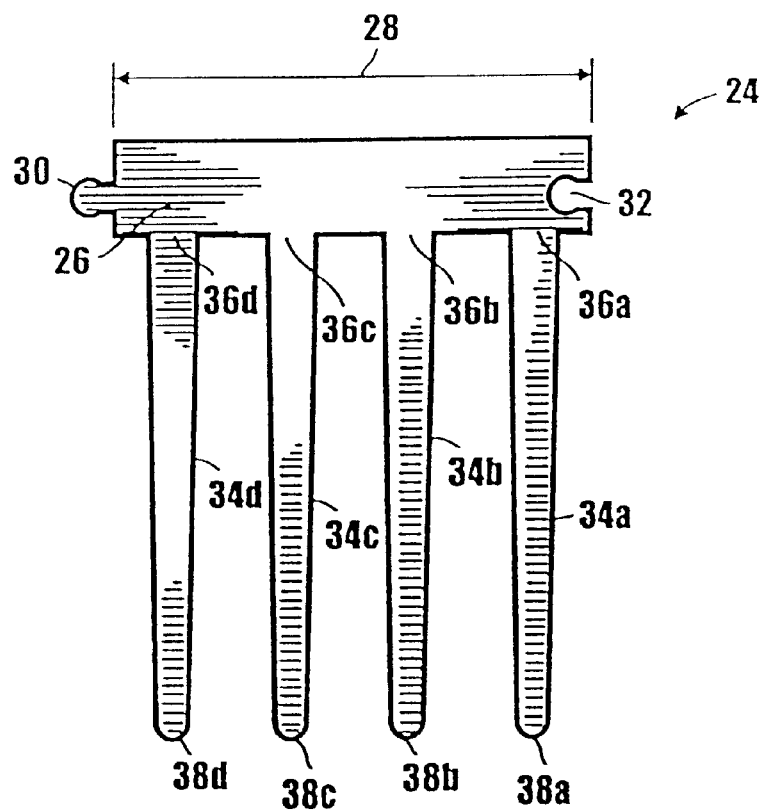
FIG. 2 is a top plan view of the device of the present invention.

FIG. 2 shows that the device 24 of the present invention has a band 26 and a plurality of elongated fingers 34a–d that are attached to band 26. Although device 24 is shown with four fingers 34a–d, this is only exemplary as there may be more or fewer fingers 34 depending on the particular need. In any case, each finger 34 has a first end 36 and a second end 38, with the first end 36 being attached to band 26 and the second end 38 extending away from band 26. As shown, the fingers 34a–d are substantially parallel to each other and the second end 38 of each finger 34 is rounded. As also shown in FIG. 2, band 26 is formed with a tab 30 and a notch 32. The length 28 of band 26 corresponds to the diameter of catheter tube 18. Preferably, band 26 with tab 30 and notch 32 and fingers 34a–d are stamped out from a single flat sheet of stainless steel.

Figure 3A:
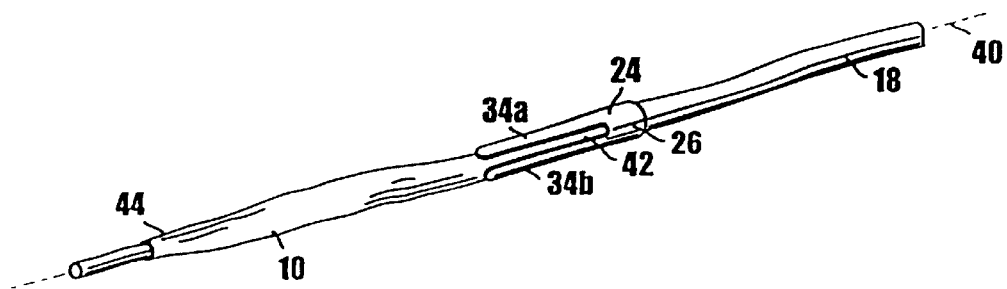
FIG. 3A is a perspective view of the device of the present invention engaged with a deflated balloon.
Figure 3B:
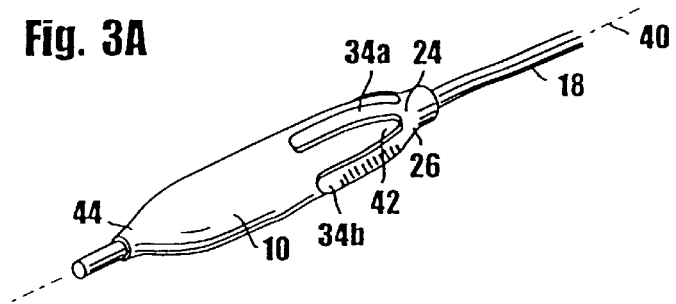
FIG. 3B is a perspective view of the device shown in FIG. 3A with the balloon inflated.

The present invention can perhaps be best appreciated by cross-referencing FIGS. 3A and 3B. Specifically, FIGS. 3A and 3B show that the balloon catheter tube 18, including the device 24, is centered on an axis 40 that is generally defined, by the longitudinal axis of the catheter tube 18. When mounted on the catheter tube 18, the band 26 is rolled so that tab 30 is engaged with notch 32 to form an annulus. As shown in FIGS. 3A and 3B, the annular band 26 is centered on axis 40 with fingers 34a and 34b extending from the band 26 in a substantially same axial direction over balloon 10.

Figure 4:
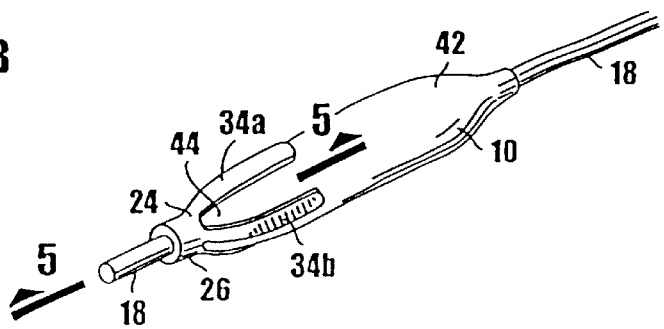
FIG. 4 is a perspective view of the device of the present invention in an alternative embodiment.
Figure 5A:
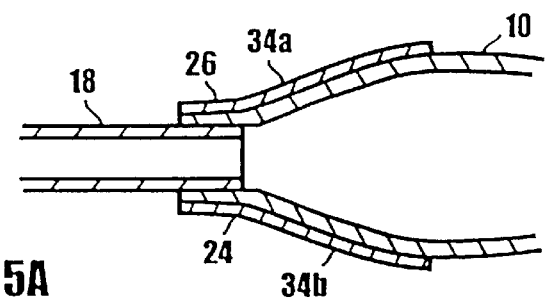
FIG. 5A is a cross-sectional view of the device of the present invention as seen along the line 5—5 in FIG. 4.
Figure 5B:
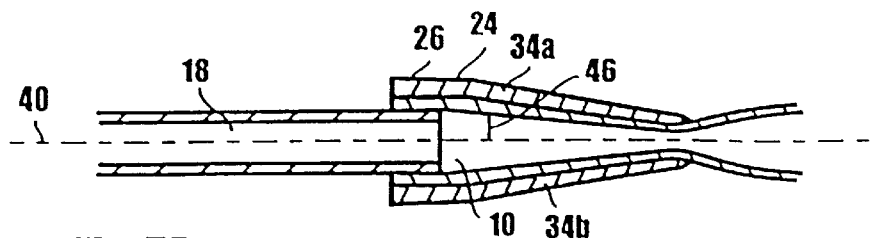
FIG. 5B is a cross-sectional view of the device shown in FIG. 5A with the balloon deflated.

In contrast to each other, FIG. 3A shows device 24 in an unstressed configuration with balloon 10 deflated. FIG. 3B, on the other hand, shows device 24 in a stressed configuration with balloon 10 inflated. For this device 24, it is an important aspect that the fingers 34a–d are not bonded to balloon 10. Consequently, the fingers 34a–d continually conform to the balloon 10 and are moveable between an unstressed configuration, as shown in FIG. 3A, and a stressed configuration, as shown in FIGS. 3B and 4. In a stressed configuration, as shown in FIGS. 3B, 4 and 5A, balloon 10 is inflated and fingers 34a and 34b urge against balloon 10 away from axis 40. In an unstressed configuration as shown in FIGS. 3A and 5B, fingers 34a–d are inclined at a slight angle 46 from the annular band 26 toward axis 40. Angle 46, as shown in FIG. 5B, is in a range from approximately five degrees to approximately fifteen degrees (5°–15°).

As indicated in FIGS. 3A and 3B, balloon 10 has a proximal end 42 and a distal end 44. In FIGS. 3A and 3B, the band 26 is mounted on catheter tube 18 proximal to balloon 10 with fingers 34a and 34b extending in a distal direction over balloon 10. Alternatively, as shown in FIG. 4, band 26 as an annulus can be mounted on catheter tube 18 distal to balloon 10 with fingers 34a and 34b extending in a proximal direction over balloon 10.

Figure 6:
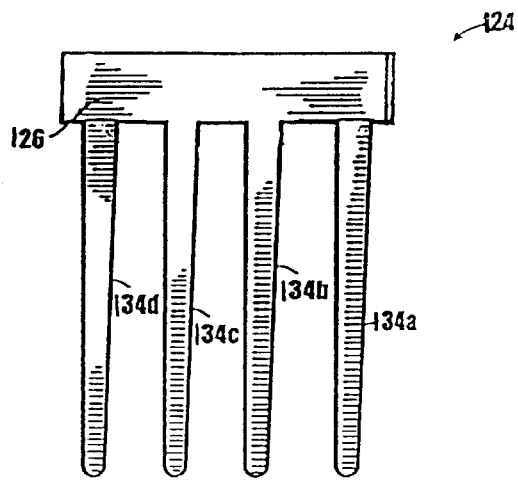
FIG. 6 is a top plan view of another embodiment of the present invention in which the band is formed with overlaps, showing the band before the band is folded into an annulus.

Referring now to FIG. 6, another embodiment of the device 124 in accordance with present invention is shown. As shown, the device 124 includes a band 126 and a plurality of elongated fingers 134a–d that extend from the band 126. With cross reference to FIGS. 6 and 7, it can be seen that the band 126 is formed with a midsection 48 that extends from midsection end 50 of midsection end 52. It can be further seen that the band 126 includes an overlap 54 that extends from the midsection end 50 to band end 56. Also, as shown, the band 126 includes an overlap 58 that extends from the midsection end 52 to band end 60.

Figure 7:
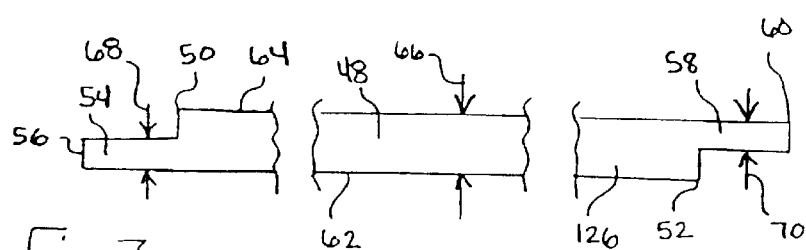
FIG. 7 is a side plan view of the embodiment shown in FIG. 6 showing the band midsection and overlaps that are formed as cantilevers.

With continued reference to FIG. 7, it can be seen that the band 126 is formed with a first side 62 and an opposed second side 64. As further shown, the midsection 48 has a midsection thickness 66 between side 62 and side 64. It can be further seen that overlap 54 is shaped as a cantilever having a substantially constant overlap thickness 68 between side 62 and side 64. Similarly, overlap 58 is shaped as a cantilever having a substantially constant overlap thickness 70 between side 62 and side 64. Preferably, as shown, overlap thickness 68 and overlap thickness 70 are both smaller than midsection thickness 66 In a particular embodiment for the present invention, overlap thickness 68 and overlap thickness 70 are both approximately half of midsection thickness 66.

Figure 8:
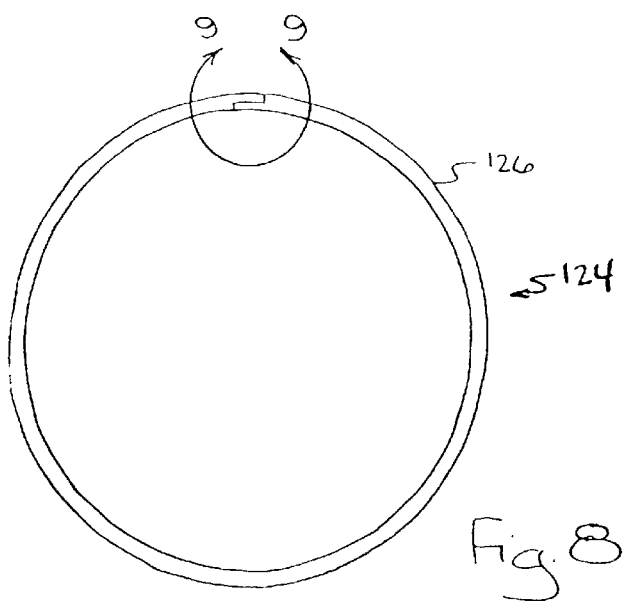
FIG. 8 is a side plan view of the band midsection and overlaps as in FIG. 6, shown after the band has been folded into an annulus and the overlaps have been juxtaposed and joined.
Figure 9:
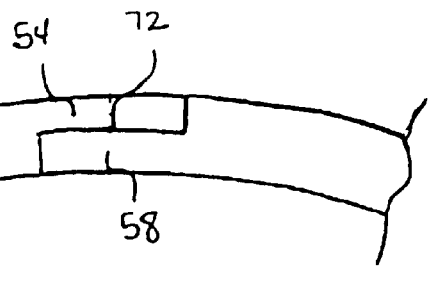
FIG. 9 is a detail, side plan view as enclosed by line 9—9 in FIG. 8 showing the overlap joint for overlaps that are formed as cantilevers.

Referring now to FIG. 8, the device 124 is shown after the band 126 has been folded into an annulus. With cross reference to FIGS. 8 and 9 it can be seen that when the band 126 has been folded into an annulus, the overlaps 54, 58 are juxtaposed. Once juxtaposed, the overlaps 54, 58 can be joined creating a joint 72. Suitable techniques for joining the overlaps 54, 58 include, but are not limited to soldering, welding to include spot welding, and adhesive bonding.

Figure 11:
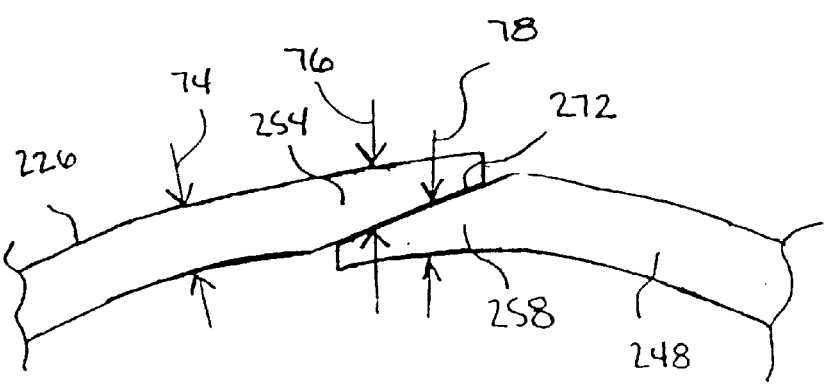
FIG. 11 is a detail, side plan view as in FIG. 9 showing the overlap joint for overlaps that are formed as tapered extensions.
Figure 10:
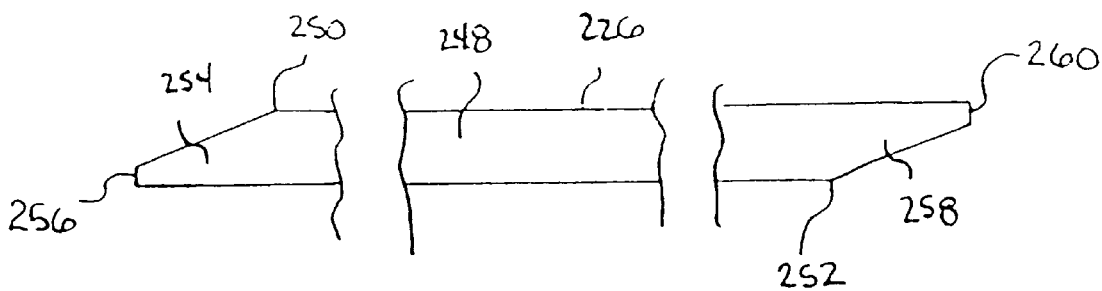
FIG. 10 is a side plan view as in FIG. 7 of another embodiment of the present invention in which the overlaps are formed as tapered extensions, shown before the band is folded into an annulus.

In another embodiment of the present invention as shown in FIGS. 10 and 11, the overlaps 254, 258 are formed as tapered extensions. When the band 226 has been folded into an annulus, the midsection 248 of the band 226 has a radial midsection thickness 74. It can be further seen that the overlap 254 has a radial overlap thickness 76 that decreases in a direction from the midsection end 250 to the band end 256. Also shown, overlap 258 has a radial overlap thickness 78 that decreases in a direction from the midsection end 252 to the band end 260. With the band 226 folded into an annulus, the overlaps 254, 258 are juxtaposed and joined together creating a joint 272. Suitable techniques for joining the overlaps 254, 258 include, but are not limited to soldering, welding to include spot welding, and adhesive bonding.

Operation

In the operation of the present invention, reference is first made to FIGS. 1 and 3A. In these Figs., the device 24 is shown attached to catheter tube 18 of a balloon catheter with the balloon 10 deflated and fingers 34a and 34b in an unstressed configuration. In its deflated configuration, balloon 10 can then be inserted through the insertion catheter 22 and advanced into the patient 14 until balloon 10 is positioned adjacent stenosis 16. Fluid from source 20 can then be infused into balloon 10 through catheter tube 18 to inflate the balloon 10 in accordance with appropriate angioplasty procedures.

Balloon 10 is infused with fluid from source 20 until fully inflated. When in an inflated configuration, as shown in FIGS. 3B, 4 and 5A, balloon 10 presses against the stenosis 16 to breakup or compact the plaque against the arterial wall. Also, with the balloon 10 inflated, fingers 34a–d have a stressed configuration and extend away from axis 40. In this configuration, the fingers 34a–d tend to urge against balloon 10 to fold the balloon 10 inwardly toward axis 40. Accordingly, when fluid is withdrawn from balloon 10, the fingers 34a–d of the device 24 return the balloon 10 to its deflated configuration, as shown in FIGS. 3A and 5B. In order to do this, the fingers 34a–d are biased toward their unstressed configuration and, thus, they assist in deflating balloon 10. In its deflated configuration, balloon 10 may be subsequently removed from the patient's artery 12.

While the particular folding spring as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A device for folding a balloon of a balloon catheter onto a catheter tube during balloon deflation, said device comprising:
    a band formed with a first side and an opposed second side, said band having a midsection with a midsection thickness between said sides and a pair of overlaps with each said overlap extending from said midsection to a respective end of said band, and wherein said band has a smaller thickness between said sides at each said end than said midsection thickness;
    a plurality of elongated fingers attached to said band;
    a means for holding said overlaps juxtaposed to configure said band as an annulus; and
    a means for mounting said annulus onto the catheter tube to position said fingers over the balloon to fold the balloon onto the catheter tube during deflation of the balloon.

2. A device as recited in claim 1 wherein the holding means is solder.

3. A device as recited in claim 1 wherein the holding means is an adhesive.

4. A device as recited in claim 1 wherein the holding means is a weld.

5. A device as recited in claim 1 wherein each said overlap is formed as a cantilever having a substantially constant thickness between said sides from said midsection to a respective said end.

6. A device as recited in claim 5 wherein each said overlap has the substantially same thickness between said sides.

7. A device as recited in claim 6 wherein the thickness of each said overlap is approximately half said midsection thickness.

8. A device as recited in claim 1 wherein each said overlap is formed as a tapered extension having a substantially uniform transition from said midsection to a respective said end.

9. A device for folding a balloon of a balloon catheter onto a catheter tube during balloon deflation, said device comprising:
    an annular shaped band having a midsection extending from a first midsection end to a second midsection end;
    a pair of overlaps with each said overlap extending from a respective said midsection end, said overlaps being juxtaposed and joined together to create a joint for said band; and
    a plurality of elongated fingers attached to said band, said fingers for interaction with the balloon to fold the balloon onto the catheter tube during deflation of the balloon.

10. A device as recited in claim 9 wherein said midsection has a substantially uniform radial thickness.

11. A device as recited in claim 9 wherein said overlaps are joined together using solder.

12. A device as recited in claim 9 wherein said overlaps are joined together using adhesive.

13. A device as recited in claim 9 wherein said overlaps are joined together by a weld.

14. A device as recited in claim 9 wherein each said overlap is formed as a cantilever having a substantially constant radial thickness and each said overlap has the substantially same radial thickness.

15. A device as recited in claim 9 wherein each said overlap is tapered having a decreasing radial thickness in a direction away from a respective said midsection end.

16. A method for manufacturing a folding spring for folding a balloon of a balloon catheter onto a catheter tube during balloon deflation, said method comprising the steps of:
    providing a band with a plurality of elongated fingers attached to said band, said band formed with a first side and an opposed second side and having a midsection with a midsection thickness between said sides, said band formed with a pair of overlaps with each said overlap extending from said midsection to a respective end of said band, and wherein said band has a smaller thickness between said sides at each said end than said midsection thickness;
    folding said band to juxtapose said overlaps; and
    joining said overlaps together to configure said band as an annulus.

17. A method as recited in claim 16 wherein said joining step comprises the step of soldering said overlaps together.

18. A method as recited in claim 16 wherein said joining step comprises the step of welding said overlaps together.

19. A method as recited in claim 16 wherein said providing step comprises the step of stamping said band and said plurality of elongated fingers from a sheet of metal.

20. A method as recited in claim 16 wherein said metal is selected from the group of metals consisting of a stainless steel allow and a Nickel-Titanium alloy.

* * * * *